United States Patent [19]

McRae

[11] Patent Number: Plant 6,426

[45] Date of Patent: Nov. 29, 1988

[54] LILY NAMED PEACH PIXIE

[75] Inventor: Edward A. McRae, Boring, Oreg.

[73] Assignee: Melridge, Inc., Gresham, Oreg.

[21] Appl. No.: 18,919

[22] Filed: Feb. 25, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new variety of lily plant of short stature bearing large clusters of upright, medium sized flowers of excellent form particularly characterized by their deep peach-pink, gold accented coloration and by their virtual lack of spots. The short stature of this plant and its medium sized, upright flowers make it especially suitable as a pot plant variety. The plant is fully clothed with moderately long leaves and its color pattern provides a lily plant silhouette that is completely new in the upright Asiatic divisions of lilies suited to forcing and mass commerical cultivation. The plant is highly resistant to disease and shows high tolerance of virus, making it an excellent garden plant, and its bulbs may be precooled and forced throughout the year for pot plant production. Also, its clone is vigorous and is a good grower and propagator.

1 Drawing Sheet

BACKGROUND OF THE NEW PLANT

My new variety of lily plant originated as a seedling selected from a group of seedlings planted by me at Sandy, Oreg., and resulting from a crossing which I made by using as the seed parent a very short, cream-colored clonal selection from the pastel hybrid strain, and as the pollen parent a red-orange flowered seedling from 'Connecticut Lemonglow'×'Red Carpet' (both unpatented), the objective of this crossing being the production of lilies in shades of pink and peach well suited to forcing for pot plant production out-of-season, a characteristic heretofore unknown in the lily breeding art.

This particular seedling was selected for propagation and test because of its short stature and medium sized flowers of deep peach-pink coloration and spotlessness and I reproduced the selected seedling by bulb scale propagation and by natural propagation from bulblets with very satisfactory results and subsequently this new plant was propagated through several successive generations by me and under my direction, which demonstrated that the novel and distinctive characteristics of the new variety hold true under asexual propagation from generation to generation and appear to be firmly fixed.

Our work with this new variety shows that it remains short and is not overly susceptible to bud abortion when forced into flower out-of-season as a pot plant and in addition, we have found that the clone possesses to a high degree the desirable characteristics of hybrid vigor, great hardiness, and disease resistance, possessing all of the desirable characteristics of excellence of form, color, and habit, as observed at Sandy, Oreg.

We have found the new variety to be well suited to forcing out-of-season when the bulbs are dug at the appropriate time and properly precooled. For example, October-dug bulbs, properly precooled and potted in January, will flower under glass in western Oregon in an average of sixty-five to seventy-five days, with no supplemental lighting and at moderate greenhouse temperatures.

DESCRIPTION OF THE DRAWING

This new hybrid lily cultivar is illustrated by the accompanying full color photographic drawing, which shows a face view of a fully opened bloom illustrating the flower form and its distinctive deep peach-pink, gold accented, and virtually spotless characteristics, the color rendition being as nearly true to that herein specified as may be reasonably obtained by conventional professional photographic procedures.

DESCRIPTION OF THE NEW PLANT

The following is a detailed description of my new lily cultivar based upon observations of plants grown at Sandy, Oreg., during the middle of 1986, the nomenclature being according to the International Lily Register (The Royal Horticultural Society of London, England, 2nd Edition, 1969) and with color designations according to The R.H.S. Colour Chart published by The Royal Horticultural Society in 1966.

THE PLANT

Origin: Seedling.

Parentage:

*Seed parent.*—A very short, cream-flowered clonal selection from the pastel hybrids strain.

*Pollen parent.*—A red-orange flowered seedling from 'Connecticut Lemonglow'×'Red Carpet' (both unpatented). po0 Classification:

*Botanic.*—Division I-A, upright Asiatic hybrid lily, according to the Horticultural Classification of Lilies, The Royal Horticultural Society of London.

*Commercial.*—Hybrid Lilium Clone.

Form: Single stem, erect and stately.

Height: About 35 to 40 cm. for stems produced by glasshouse forcing of bulbs about 18 to 20 cm. in circumference; provided that their light levels are adequate. Low light levels may cause "stretching".

Growth: Vigorous and upright.

Foliage:

*Quantity.*—Abundant.

*Size of leaf.*—About 8 to 15 cm. long and about 0.5 cm. wide.

*Shape of leaf.*—Lanceolate with acuminate tip and entire margins.

*Texture.*—Leathery.

*Aspect.*—Glossy and lightly pubescent.

*Color.*—Dark green and lighter on the under side.

The bulb:

*Size.*—Various, ranging to 25 cm. in circumference in commercial use.

*Color.*—White.

THE BUD

Form: Long ovoid with obtuse tip and base.

Size: About 8 to 9 cm. long and about 5 cm. in circumference just prior to opening.

Opening rate: The bud opens slowly, taking about one hour in response to morning light.

Color: Soft to medium peach-pink with a flush of green along the midribs and at the tip, just prior to opening and as the tepals unfurl.

Peduncle:

*Length.*—About 4 to 6 cm., in average, but may elongate if light levels are too low or if the bulbs have been improperly stored prior to forcing.

*Color.*—Dark green.

THE FLOWER

Blooming habit: Once annually, flowering profusely in midseason.

Size: The flowers average about 13 to 15 cm. in diameter.

Borne: In a single compact raceme having 6 to 9 buds from a bulb about 12 to 16 cm. in circumference.

Shape: Cup-shaped when first opening and flattening somewhat as the tepals recurve during the second day.

Tepalage: Normal, with six imbricated tepals in hexagonal arrangement.

*Tepal size.*—The outer tepals average about 3 cm. wide and the inner tepals average about 3.5 cm. wide.

*Color.*—The flowers are distinguished by their broad tepalled form and thick substance and especially by their deep peach-pink coloration, the peach color being created by purple-pink pigments in the upper cell layers, covering softer orange pigments in the center cell layers; this combination appearing to the eye and to the color chart as orange-red, 35B-C. A flush of gold, 23A-B through 26A-B, about 1 cm. wide extends down the midrib about 2 to 3 cm. from the nectaries. The nectaries are a soft peach, overlaid with white pubescence, this combination appearing to the eye and to the color chart as orange-red, 35B-C.

*Spotting.*—The tepals are virtually unspotted; a few extremely tiny, deep magenta spots are parallel with the nectaries on each tepal. Spotting, however, is extremely inconspicuous.

*Longevity.*—The tepals stay on the stems about three weeks.

Pedicel:

*Length.*—About 4 to 8 cm., in average.

*Form.*—Sturdy and ascending up to 60 degrees from the horizontal.

*Color.*—Dark green and lightly pubescent.

Color changes: The flowers may become slightly more apricot toned under conditions of great heat and strong light. With very cool temperatures and moderate light levels, the flowers may become more pink toned. When the flowers age, they fade slightly to red, 37A-B.

Disease resistance: The flower and plant are resistant to disease and in particular, they are resistant to Fusarium bulb rot and Botrytis blight.

Lasting quality: The flowers are long lasting, both on the plant and as cut flowers.

REPRODUCTIVE ORGANS

Stamens:

*Number.*—Six, in arrangement typical of genus Lilium.

*Pollen and anthers (dehisced).*—Greyed orange, 168A.

*Filaments.*—Length: About 5 cm. Color: Soft red, 39B-C.

Pistil:

*Number.*—One.

*Style.*—Length: About 5 cm.

*Stigma.*—Size: Medium. Color: Deep plum.

Character of ovary: The ovary has the typical characteristics of the genus Lilium.

THE FRUIT

Fertility: The fruit is fertile.

Shape: Ovoid.

Color at maturity: Soft brown, sometimes overlaid with soft plum.

This new lily variety most closely resembles 'Peachblush' (unpatented) but it has a deeper and more uniform coloration with only a few extremely inconspicuous, tiny spots and a more compact inflorescence with shorter pedicels, a shorter height, and more abundant and narrower leaves than the variety 'Peachblush'. It is also more reliable and uniform in its forcing performance than the variety 'Peachblush'.

I claim:

1. A new and distinctive variety of Asiatic hybrid lily, substantially as herein shown and described, characterized by its virtually unspotted, gold accented, deep peach-pink flowers and by its short stemmed, longer, and more abundant leaves and an upright flowering silhouette; this plant has a high resistance to disease and a high tolerance to virus; its vigorous growth habit and rapid natural propagation together with its versatility both as a garden plant and as a pot plant variety make it well suited to forcing into flower out of season from properly precooled bulbs.

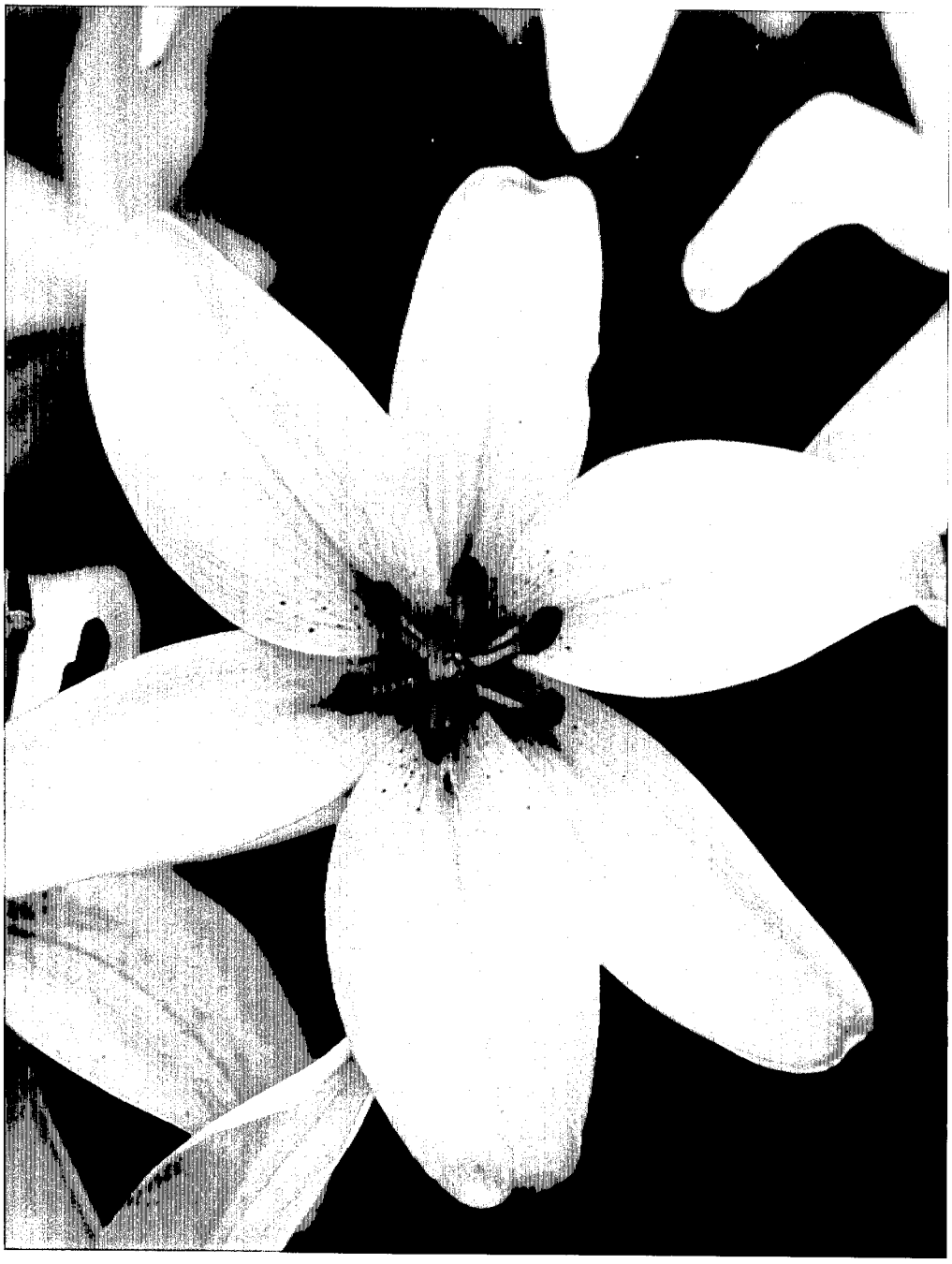

* * * * *